(12) United States Patent
Jennings et al.

(10) Patent No.: US 7,304,158 B2
(45) Date of Patent: Dec. 4, 2007

(54) METHOD FOR MAKING 2-(7-CHLORO-1,8-NAPHTHYRIDINE- 2-YL)-3-(5-METHYL-2-OXO-HEXYL)-1-ISOINDOLINONE)

(75) Inventors: Sandra Marie Jennings, Hamilton, MI (US); Timothy Lee Stuk, Holland, MI (US)

(73) Assignee: Indevus Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 11/411,952

(22) Filed: Apr. 27, 2006

(65) Prior Publication Data

US 2006/0194830 A1    Aug. 31, 2006

Related U.S. Application Data

(60) Division of application No. 11/206,144, filed on Aug. 18, 2005, now Pat. No. 7,057,047, which is a continuation of application No. 10/400,780, filed on Mar. 27, 2003, now Pat. No. 6,949,653.

(60) Provisional application No. 60/368,609, filed on Mar. 29, 2002.

(51) Int. Cl.
 *C07D 471/02* (2006.01)
(52) U.S. Cl. .................................... 546/122
(58) Field of Classification Search ................. 546/122
 See application file for complete search history.

(56) References Cited

U.S. PATENT DOCUMENTS

| 4,220,646 A | 9/1980 | Cotrel et al. |
| 4,960,779 A | 10/1990 | Bourzat et al. |
| 5,498,716 A | 3/1996 | David-Comte et al. |
| 5,532,228 A | 7/1996 | Neef et al. |
| 5,599,936 A | 2/1997 | Barreau et al. |
| 6,949,653 B2* | 9/2005 | Jennings et al. ............ 546/122 |
| 7,057,047 B2* | 6/2006 | Jennings et al. ............ 546/122 |

FOREIGN PATENT DOCUMENTS

| WO | WO 93/01187 | 1/1993 |
| WO | WO 93/01188 | 1/1993 |
| WO | WO 93/01189 | 1/1993 |
| WO | WO 93/05041 | 3/1993 |
| WO | WO 93/11125 | 6/1993 |
| WO | WO 93/13098 | 7/1993 |
| WO | WO 94/05663 | 3/1994 |

OTHER PUBLICATIONS

Newkome et al., Journal of Organic Chemistry, "Chemistry of heterocyclic compounds. 61. synthesis and conformational studies of macrocycles possessing 1,8-or 1,5-Naphthyridino subunits connected by carbon-oxygen bridges", 1981, vol. 46, pp. 833-839.*

* cited by examiner

*Primary Examiner*—Margaret D. Seaman
*Assistant Examiner*—Niloofar Rahmani
(74) *Attorney, Agent, or Firm*—Gilberto M. Villacort; Steven M. Reid; Foley & Lardner LLP

(57) ABSTRACT

The present invention relates to methods for making racemic 2-(7-chloro -1,8-naphthyridin-2-yl)-3-(5-methyl-2-oxo-hexyl)-1-isoindolinone and (+)-2-(7 -chloro-1,8-naphthyridine-2-yl)-3-(5-methyl-2-oxo-hexyl)-1-isoindolinone.

5 Claims, No Drawings

METHOD FOR MAKING 2-(7-CHLORO-1,8-NAPHTHYRIDINE-2-YL)-3-(5-METHYL-2-OXO-HEXYL)-1-ISOINDOLINONE)

This is a divisional of application Ser. No. 11/206,144, filed Aug. 18, 2005, which is a continuation of application Ser. No. 10/400,780, filed Mar. 27, 2003, now U.S. Pat. No. 6,949,653 which claims benefit of application No. 60/368,609, filed Mar. 29, 2002, the disclosures of which are incorporated by reference in their entirety herein.

FIELD OF THE INVENTION

The present invention relates to methods for making racemic 2-(7-chloro-1,8-naphthyridine-2-yl)-3-(5-methyl-2-oxo-hexyl)-1-isoindolinone and (+)-2-(7-chloro-1,8-naphthyridine-2-yl)-3-(5-methyl-2-oxo-hexyl)-1-isoindolinone.

BACKGROUND OF THE INVENTION

The compound (+)-2-(7-chloro-1,8-naphthyridine-2-yl)-3-(5-methyl-2-oxo-hexyl)-1-isoindolinone, also called pagoclone, is a GABA (gamma amino butyric acid) receptor ligand that is presently being evaluated in human clinical studies for the treatment of generalized anxiety disorder and panic disorder.

Pagoclone can also be used to treat obsessive-compulsive disorder, acute stress disorder, post traumatic stress disorder, social anxiety disorder, somatization disorder, specific social phobia, premenstrual dysphoric disorder, anxiety associated with a medical condition, adjustment disorder with anxious mood, dysthymia, specific phobia or fibromyalgia.

U.S. Pat. No. 4,960,779, issued Oct. 2, 1990, relates to pyrrole derivatives and compositions comprising pyrrole derivatives, including pagoclone, and to methods of producing an anxiolytic, hypnotic, anticonvulsant, antiepileptic or muscle relaxant therapeutic effect that comprises administering a pyrrole derivative.

The present invention provides a convenient method for making racemic 2-(7-chloro-1,8-naphthyridine-2-yl)-3-(5-methyl-2-oxo-hexyl)-1-isoindolinone and (+)-2-(7-chloro-1,8-naphthyridine-2-yl)-3-(5-methyl-2-oxo-hexyl)-1-isoindolinone.

SUMMARY OF THE INVENTION

The present invention provides methods of making racemic 2-(7-chloro-1,8-naphthyridin-2-yl)-3-(5-methyl-2-oxo-hexyl)-1-isoindolinone, the methods comprising the steps of:

a) reacting 2,6-diaminopyridine with malic acid and sulfuric acid to form 2-amino-7-hydroxy-1,8-naphthyridine sulfuric acid salt;

b) reacting 2-amino-7-hydroxy-1,8-naphthyridine sulfuric acid salt with a phthalyl reactant in a solvent to form phthalimidyl naphthyridine 2

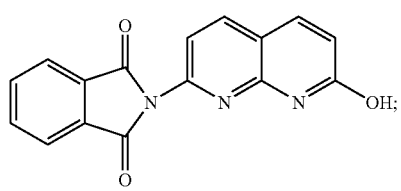

c) reacting phthalimidyl naphthyridine 2 with a chlorinating agent to form chloride 3

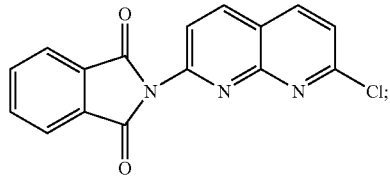

d) reacting chloride 3 with a reducing agent to form hydroxyindolinone 4

e) reacting hydroxyindolinone 4 with a 5-methyl-2-oxo-hexyl derivative to form racemic 2-(7-chloro-1,8-naphthyridin-2-yl)-3-(5-methyl-2-oxohexyl)-1-isoindolinone.

In a preferred embodiment of the methods, in step b the phthalyl reactant is phthalic anhydride; in step c the chlorinating agent is phosphorus oxychloride; in step d the reducing agent is potassium borohydride; and in step e the 5-methyl-2-oxo-hexyl derivative is [(5-methyl-2-oxo)-hexyl]triphenylphosphonium bromide.

Also provided are methods of making (+)-2-(7-chloro-1,8-naphthyridin-2-yl)-3-(5-methyl-2-oxohexyl)-1-isoindolinone, the methods comprising the steps of:

a) reacting 2,6-diaminopyridine with malic acid and sulfuric acid to form 2-amino-7-hydroxy-1,8-naphthyridine sulfuric acid salt;

b) reacting 2-amino-7-hydroxy-1,8-naphthyridine sulfuric acid salt with a phthalyl reactant in a solvent to form phthalimidyl naphthyridine 2

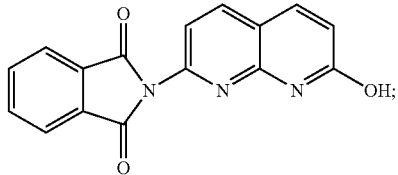

c) reacting phthalimidyl naphthyridine 2 with a chlorinating agent to form chloride 3

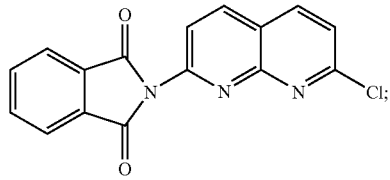

d) reacting chloride 3 with a reducing agent to form hydroxyindolinone 4

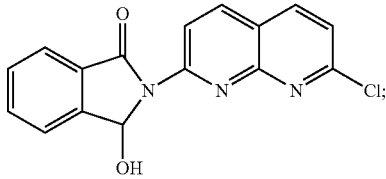

e) reacting hydroxyindolinone 4 with a 5-methyl-2-oxohexyl derivative to form racemic 2-(7-chloro-1,8-naphthyridin-2-yl)-3-(5-methyl-2-oxohexyl)-1-isoindolinone; and f) resolving racemic 2-(7-chloro-1,8-naphthyridin-2-yl)-3-(5-methyl-2-oxohexyl)-1-isoindolinone to provide (+)-2-(7-chloro-1,8-naphthyridin-2-yl)-3-(5-methyl-2-oxohexyl)-1-isoindolinone.

In a preferred embodiment of the methods wherein the racemic 2-(7-chloro-1,8-naphthyridin-2-yl)-3-(5-methyl-2-oxohexyl)-1-isoindolinone is resolved to provide (+)-2-(7-chloro-1,8-naphthyridin-2-yl)-3-(5-methyl-2-oxohexyl)-1-isoindolinone, the resolution comprises the steps of:

g) reacting racemic 2-(7-chloro-1,8-naphthyridin-2-yl)-3-(5-methyl-2-oxohexyl)-1-isoindolinone with a base to form acid 6

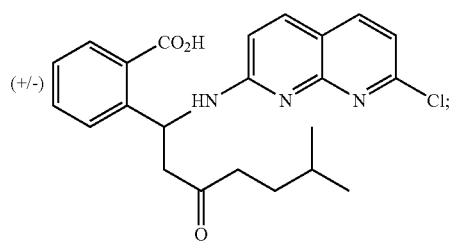

h) reacting acid 6 with (+)-ephedrine to form salt 6a

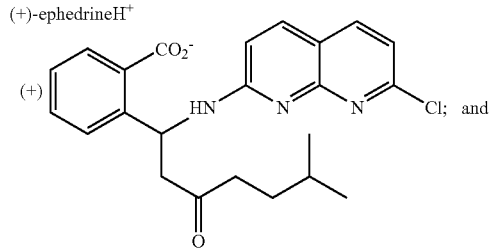

i) reacting salt 6a with an amide forming reagent to form (+)-2-(7-chloro-1,8-naphthyridin-2-yl)-3-(5-methyl-2-oxohexyl)-1-isoindolinone.

In a preferred embodiment of the resolution, the base in step g is potassium hydroxide; and in step i the amide forming reagent is carbonyldiimidazole.

Also provided is the compound 2-amino-7-hydroxy-1,8-naphthyridine sulfuric acid salt.

Also provided are methods of making 2-amino-7-hydroxy-1,8-naphthyridine sulfuric acid salt, the methods comprising the step of reacting 2,6-diaminopyridine with malic acid and sulfuric acid to form 2-amino-7-hydroxy-1,8-naphthyridine sulfuric acid salt.

Also provided are methods of making racemic 2-(7-chloro-1,8-naphthyridin-2-yl)-3-(5-methyl-2-oxohexyl)-1-isoindolinone, the methods comprising the steps of:

a) reacting 2-amino-7-hydroxy-1,8-naphthyridine sulfuric acid salt with a phthalyl reactant in a solvent to form phthalimidyl naphthyridine 2

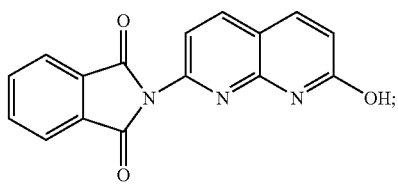

b) reacting phthalimidyl naphthyridine 2 with a chlorinating agent to form chloride 3

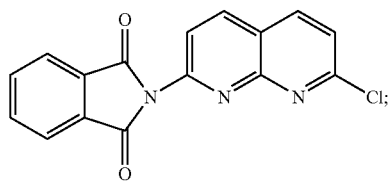

c) reacting chloride 3 with a reducing agent to form hydroxyindolinone 4

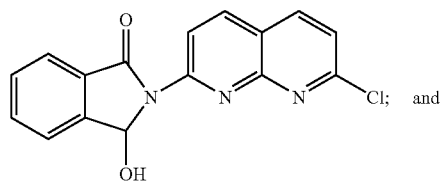

d) reacting hydroxyindolinone 4 with a 5-methyl-2-oxohexyl derivative to form racemic 2-(7-chloro-1,8-naphthyridin-2-yl)-3-(5-methyl-2-oxohexyl)-1-isoindolinone.

Also provided are methods of making racemic 2-(7-chloro-1,8-naphthyridin-2-yl)-3-(5-methyl-2-oxohexyl)-1-isoindolinone, the methods comprising the steps of:

a) reacting phthalimidyl naphthyridine 2

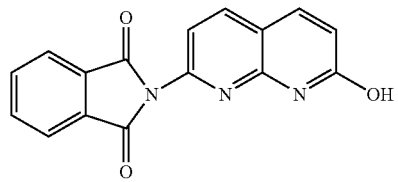

with a chlorinating agent to form chloride 3

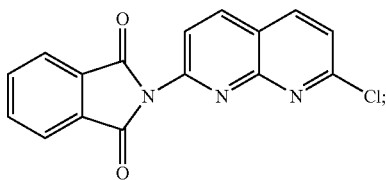
3 b) reacting chloride 3 with a reducing agent to form hydroxyindolinone 4

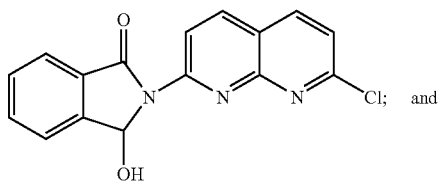
4 c) reacting hydroxyindolinone 4 with a 5-methyl-2-oxo-hexyl derivative to form racemic 2-(7-chloro-1,8-naphthyridin-2-yl)-3-(5-methyl-2-oxohexyl)-1-isoindolinone.

Also provided are methods of making racemic 2-(7-chloro-1,8-naphthyridin-2-yl)-3-(5-methyl-2-oxohexyl)-1-isoindolinone, the methods comprising the steps of:

a) reacting chloride 3

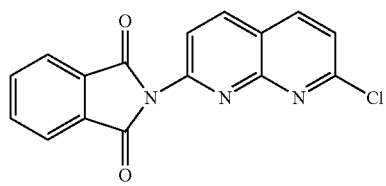
3 with a reducing agent to form hydroxyindolinone 4

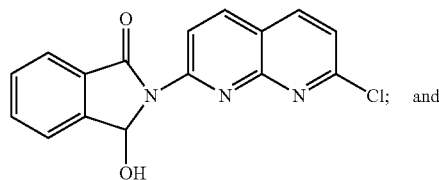
4 b) reacting hydroxyindolinone 4 with a 5-methyl-2-oxo-hexyl derivative to form racemic 2-(7-chloro-1,8-naphthyridin-2-yl)-3-(5-methyl-2-oxohexyl)-1-isoindolinone.

Also provided are methods of making racemic 2-(7-chloro-1,8-naphthyridin-2-yl)-3-(5-methyl-2-oxohexyl)-1-isoindolinone, the method comprising the step of reacting hydroxyindolinone 4

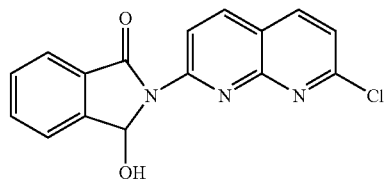
4 with a 5-methyl-2-oxo-hexyl derivative to form racemic 2-(7-chloro-1,8-naphthyridin-2-yl)-3-(5-methyl-2-oxohexyl)-1-isoindolinone.

DETAILED DESCRIPTION OF THE INVENTION

The present invention provides methods for making racemic 2-(7-chloro-1,8-naphthyridine-2-yl)-3-(5-methyl-2-oxo-hexyl)-1-isoindolinone and then resolving the racemic 2-(7-chloro-1,8-naphthyridine-2-yl)-3-(5-methyl-2-oxo-hexyl)-1-isoindolinone to provide (+)-2-(7-chloro-1,8-naphthyridine-2-yl)-3-(5-methyl-2-oxo-hexyl)-1-isoindolinone, which is called pagoclone.

The present method is illustrated in Scheme 1 below.

Scheme 1

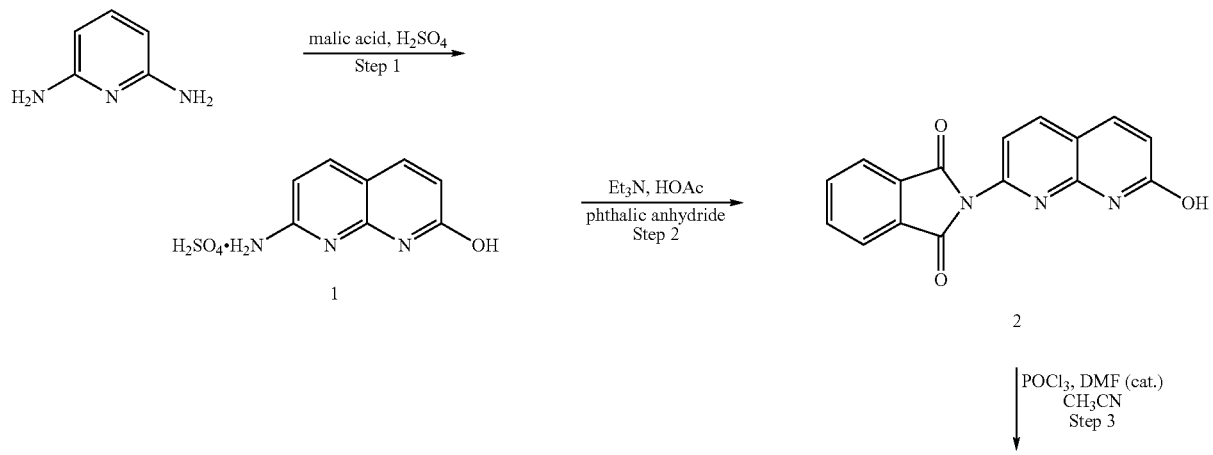

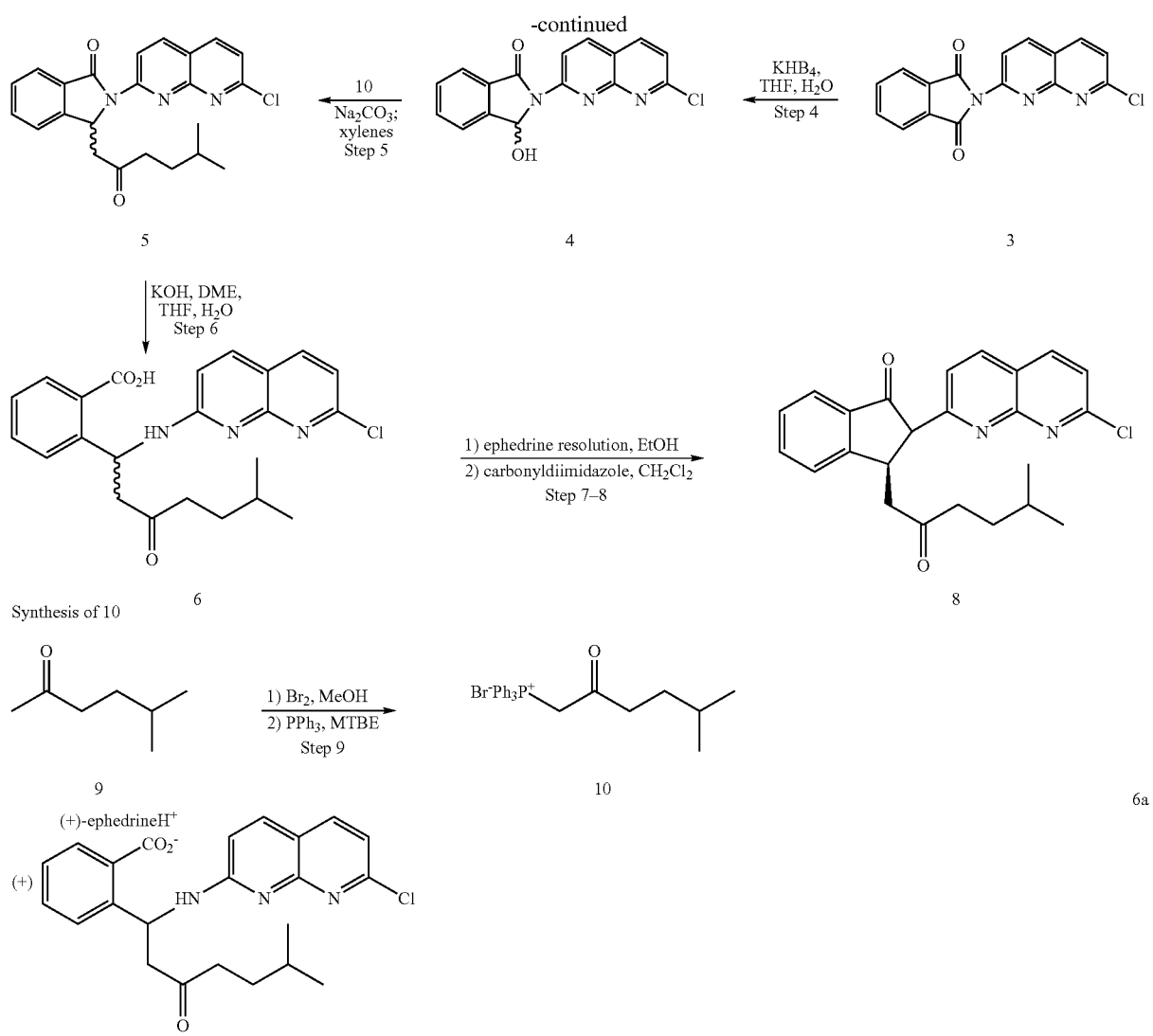

Synthesis of 10

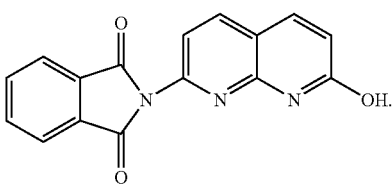

Step 1

In step 1 of the method, commercially available 2,6-diaminopyridine (e.g., Aldrich, Milwaukee, Wis.) is reacted with malic acid in sulfuric acid to provide 2-amino-7-hydroxy-1,8-naphthyridine sulfuric acid salt. It is noted that 2-amino-7-hydroxy-1,8-naphthyridine free base is described in S. Carboni et al., Gazz. Chim. Ital., 95, 1498 (1965).

2-Amino-7-hydroxy-1,8-naphthyridine sulfuric acid salt (1)

2,6-Diaminopyridine (167 g, 1.53 mol) was added in portions to sulfuric acid (1.14 kg, 11.7 mol) at 40° C. The temperature of the solution was maintained at 40-50° C. during the addition with a water bath. When all of the 2,6-diaminopyridine was dissolved, the solution was cooled to 20° C. Malic acid (206 g, 1.53 mol) was added to the solution and the reaction mixture was gradually heated to 110° C. over 90 minutes. The mixture was stirred at 110-120° C. for one hour, cooled to room temperature, and poured slowly into a cold brine solution (167 g NaCl, 1.6 kg ice water). The quenched mixture was stirred at room temperature for one hour and filtered. The material was washed with hexanes (335 mL) and dried at 60° C. under vacuum to yield 2-amino-7-hydroxy-1,8-naphthyridine sulfuric acid salt as a yellow solid: 354 g, 89% yield; MS (DCI) M+1 at 162, 100%; $^1$H NMR (200 MHz, DMSO-$d_6$) δ 4.32 (br. s, 5H, —OH, —NH$_2$, H$_2$SO$_4$), 6.41 (d, J=9.0 Hz, 1H, C6), 6.56 (d J=9.0 Hz, 1H, C5), 7.85 (d J=6.6 Hz, 1H, C3), 7.91 (d J=6.6 Hz, 1H, C4).

Steps 2-4

In step 2, 2-amino-7-hydroxy-1,8-naphthyridine sulfuric acid salt is reacted with a phthalyl reactant to form phthalimidyl naphthyridine 2

The reaction is typically conducted in a solvent, preferably acetic acid, and a base is added. The base is selected from the bases that are strong enough to deprotonate the sulfuric acid salt, but which do not destroy the phthalyl reactant. Suitable bases include di, tri and aryl substituted amines, and a preferred base is triethylamine. The phthalyl reactant is a reagent that reacts with the amine group of the 2-amino-7-hydroxy-1,8-naphthyridine sulfuric acid salt to provide the phthalimidyl naphthyridine 2. Examples of suitable phthalyl reactants include phthalyl chloride, phthalic acid and phthalic acid esters. A preferred phthalyl reactant is phthalic anhydride, and a preferred base for use with phthalic anhydride is triethylamine. The phthalimidyl naphthyridine 2 can also be made in a procedure analogous to that disclosed in U.S. Pat. No. 4,220,646.

In step 3, phthalimidyl naphthyridine 2 is reacted with a chlorinating agent to form chloride 3

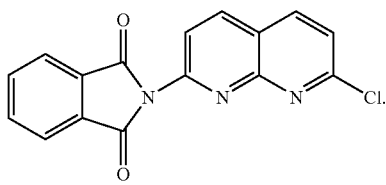

3

Chlorinating agents that convert the hydroxy group of the phthalimidyl naphthyridine to chlorine are required. Suitable chlorinating agents include, but are not limited to, thionyl chloride, cyanuric chloride, hydrochloric acid, phosphorus pentachloride, phosphorus trichloride and oxalyl chloride. A preferred chlorinating agent is phosphorus oxychloride. The chlorination can typically be run in a polar, aprotic solvent or can be run in neat phosphorus oxychloride. A preferred chlorination comprises the use of acetonitrile as the solvent and phosphorus oxychloride as the chlorinating agent. A catalytic amount of dimethlyformaminde is also used. The chloride 3 can also be made in a procedure analogous to that disclosed in U.S. Pat. No. 4,220,646.

In step 4, the chloride 3

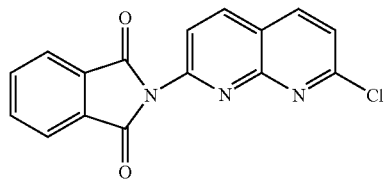

3 is reduced with a reducing agent to provide hydroxyindolinone 4

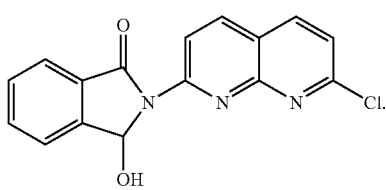

4

The reducing agent can be any compound that reduces the carbonyl group on the phthalyl ring to an alcohol. Examples of preferred reducing agents include salts of borohydride, borane and substituted boranes. A preferred borohydride salt is potassium borohydride. The solvent can be an alcohol or an ether or any other solvent that is compatible with the chloride and the reducing agent. When the reducing agent is potassium borohydride, a preferred solvent is water. It is noted that steps 3 and 4 can be run sequentially without isolation of intermediate products. The hydroxyindolinone 4 can also be made in a procedure analogous to that disclosed in U.S. Pat. No. 4,220,646.

2-N-Phthalimidyl-7-hydroxy-1,8-naphthyridine (2)

2-Amino-7-hydroxy-1,8-naphthyridine sulfuric acid salt (5.5 g) and phthalic anhydride (8.3 g) were stirred in acetic acid (27 mL). The reaction was cooled in an ice bath while triethylamine (11 mL) was added at a rate such that the batch temperature did not exceed 30° C. After all of the triethylamine was added, the reaction was heated at about 115° C. for 5 hrs. The reaction was cooled to about 25° C. and quenched with methanol (30 mL). The product was filtered and washed with methanol (30 mL). The product was dried under vacuum at 60° C. This afforded 5.9 g of 2-N-phthalimidyl-7-hydroxy-1,8-naphthyridine 2 (95% yield). $^1$H-NMR: δ 12.45 (s, 1H), 8.43 (d, J=8.1 Hz, 1H), 8.09 (m, 5H), 7.49 (d, J=8.1, 1H), 6.74 (d, J=9.5, 1H); CI (MS) M+1 at 292, 100%.

N-(7-Chloro-1,8-naphthyridin-2-yl)3-hydroxyindolinone (4)

Phosphorus oxychloride (83.9 g, 547 mmol) was added to a refluxing slurry of 2-N-phthalimidyl-7-hydroxy-1,8-naphthyridine (140 g, 481 mmol) in acetonitrile (1.05 L) and N,N-dimethylformamide (8.87 g, 121 mmol). The reaction mixture was refluxed for 4 hours and cooled to 3° C. Aqueous potassium hydroxide (45%, 109 mL, 1.28 mol) was added over 30 minutes, keeping the internal temperature below 25° C. The mixture was cooled to 3° C. Potassium borohydride (84 g, 1.56 mol) was added slowly as a solution in water (700 mL), maintaining the reaction temperature below 35° C. The mixture was heated to 35-40° C. for 1 hour and cooled to room temperature. Aqueous acetic acid (385 mL acetic acid, 350 mL water) was added followed by glacial acetic acid (875 mL). The mixture was stirred for 15 minutes and filtered. The material was washed with water (350 mL), methanol (350 mL), water (350 mL) and methanol (350 mL). It was dried at 60° C. under vacuum to yield N-(7-chloro-1,8-naphthyridin-2-yl)3-hydroxyindolinone as a light yellow solid: 140.1 g, 94% yield; MS (DCI) M+1 at 312, 100%; $^{13}$C NMR (101 MHz, DMSO-$d_6$) δ 80.74 (C2) 115.98 (C19) 119.068 (C17) 121.91 (C15) 123.39 (C9) 124.10 (C6) 129.90 (C8) 130.23 (C4) 133.90 (C7) 139.40 (C18) 140.53 (C16) 144.45 (C3) 152.69 (C12) 153.06 (C10) 153.77 (C14) 166.43 (C5).

Step 5

In step 5, N-(7-chloro-1,8-naphthyridin-2-yl)3-hydroxyindolinone is reacted with a 5-methyl-2-oxo-hexyl derivative to form racemic 2-(7-chloro-1,8-naphthyridin-2-yl)-3-(5-methyl-2-oxohexyl)-1-isoindolinone. The 5-methyl-2-oxo-hexyl derivative can be any derivative of 5-methyl-2-oxo-hexane that provides for racemic 2-(7-chloro-1,8-naphthyridin-2-yl)-3-(5-methyl-2-oxohexyl)-1-isoindolinone. A preferred 5-methyl-2-oxo-hexyl derivative is a [(5-methyl-2-oxo)-hexyl]triphenylphosphonium halide, with the bromide being preferred. The synthesis of [(5- methyl-2-oxo)-hexyl]triphenylphosphonium bromide is illustrated below. The reaction is typically run in an aprotic solvent at a temperature greater than or equal to about 100° C., and the reaction utilizes a base that is capable of deprotonating the phosphonium salt. A preferred base is sodium carbonate. Examples of additional suitable bases are carbonate salts, hydroxide salts and alkoxide salts.

Racemic-2-(7-chloro-1,8-naphthyridin-2-yl)-3-(5-methyl-2-oxo-hexyl)-1-isoindolinone (5).

To a reactor was charged water (330 L), sodium carbonate (34 kg), [(5-methyl-2-oxo)-hexyl]triphenylphosphonium bromide (10) (99 kg), and xylenes (390 kg). The two-phase system was stirred for 30 minutes at 20° C. The aqueous layer was removed and N-(7-chloro-1,8-naphthyridin-2-yl)3-hydroxyindolinone (159 kg) was added. The reaction was heated to 136° C. (with distillation of residual water) and held at that temperature for 24 hours. The reaction was cooled to 90° C. and the xylenes were removed via vacuum distillation. To the residue was charged isopropanol (650 L). The slurry was heated to reflux, cooled to less than 5° C., and isolated by filtration. Each load was washed with isopropanol (200 L) and methanol (100 L). Vacuum drying at 60° C. afforded 170 kg (82% yield) of crystalline racemic-2-(7-chloro-1,8-naphthyridin-2-yl)-3-(5-methyl-2-oxo-hexyl)-1-isoindolinone. APCI/MS: M+H$^+$ at 408, 100%. M.P. 173-4° C.

[(5-Methyl-2-oxo)-hexyl]triphenylphosphonium bromide (10)

A solution of methanol (760 mL) and 5-methy-2-hexanone (9), which can be obtained from Eastman Chemical Company, Kingsport, Tenn., (152 mL, 1.15 mol) was cooled to 0-5° C. Bromine (53 mL, 1.03 mol) was added in one portion. The reaction was stirred at about 5° C. for 50 minutes. After the exotherm was completed (about 90 minutes), the reaction was quenched with water (132 mL) and stirred for about 30 minutes. Methyl tert-butyl ether (MTBE, 1325 mL) was added. The reaction was washed with 700 mL brine solution (238 g NaCl dissolved in 1325 mL H$_2$O). The organic layer was then washed with 700 mL sodium bicarbonate solution (31.8 g NaHCO$_3$ in 663 mL H$_2$O). The organic layer was then washed with another brine solution as above. The solvent was removed under vacuum and additional MTBE (663 mL) was added to the remaining organic residue. This MTBE was also removed under vacuum. The residual oil was then dissolved in MTBE (340 mL).

Triphenylphosphine (270.2 g, 1.03 mol) was dissolved in MTBE (340 mL). The bromo ketone solution was added to this solution and allowed to react at 20° C. for 16 hours. The resulting white precipitate was filtered and dried under vacuum at 40° C. This afforded 273.1 g (58% yield) of [(5-methyl-2-oxo)-hexyl]triphenylphosphonium bromide. $^1$H-NMR: δ 7.87 (m, 15H), 5.66 (dd, J=2.9, 12.8, 2H), 2.71 (m, 2H), 1.35 (m, 3H), 0.80 (d, J=6.2, 6H); CI (MS) M at 455, 100%.

[(5-Methyl-2-oxo)-hexyl]triphenylphosphonium bromide can also be made in a method analogous to that disclosed in U.S. Pat. No. 5,532,228.

Step 6

In step 6, the lactam ring of racemic-2-(7-chloro-1,8-naphthyridin-2-yl)-3-(5-methyl-2-oxo-hexyl)-1-isoindolinone is opened to form racemic-2-[1-(7-chloro-1,8-naphthyridin-2-ylamino)-6-methyl-3-oxo-heptyl]-benzoic acid. This type of reaction is described in U.S. Pat. No. 5,498,716.

Racemic-2-[1-(7-Chloro-1,8-naphthyridin-2-ylamino)-6-methyl-3-oxo-heptyl]-benzoic acid (6)

To a reactor was charged racemic-2-(7-chloro-1,8-naphthyridin-2-yl)-3-(5-methyl-2-oxo-hexyl)-1-isoindolinone (170 kg), 1,2-dimethoxyethane (730 L), tetrahydrofuran (THF, 990 L). The slurry was heated to 30° C. and a solution of potassium hydroxide (140 Kg) in water (1730 L) was added. The slurry was stirred at 34° C. for 34 hours. The solution was cooled to 20° C. and the lower aqueous layer was removed and replaced with water (1000 L). The solution was adjusted to pH 9.0 with 4N hydrochloric acid. The solution was vacuum distilled at 30° C. to remove the THF. Water (550 L) was added and the pH of the reaction was adjusted to 11.5 with 2N potassium hydroxide. The solution was filtered to remove residual racemic-2-(7-chloro-1,8-naphthyridin-2-yl)-3-(5-methyl-2-oxo-hexyl)-1-isoindolinone. To the liquors was added methylene chloride (1200 L) and the pH was adjusted to 1.4 with 4N HCl. The aqueous layer was removed. The organic layer was washed with water (700 L) and the water was discarded. The organic layer was concentrated under vacuum and replaced with methanol (500 L). The slurry was cooled to 10° C., water was added (500 L), and the mixture was cooled to 0° C. The resulting precipitate was isolated by filtration and dried under vacuum at 50° C. to afford 150 kg (85%) of racemic-2-[1-(7-chloro-1,8-naphthyridin-2-ylamino)-6-methyl-3-oxo-heptyl]-benzoic acid as a white solid. DCI/MS: M+H$^+$ at 426, 100%. M.P. 173-4° C. UV maxima at 236 nm, 268 nm, and 353 nm.

Steps 7-8

A method for resolving racemic-2-[1-(7-chloro-1,8-naphthyridin-2-ylamino)-6-methyl-3-oxo-heptyl]-benzoic acid is described in U.S. Pat. No. 5,498,716. In the first step of the resolution, racemic-2-[1-(7-chloro-1,8-naphthyridin-2-ylamino)-6-methyl-3-oxo-heptyl]-benzoic acid is reacted with a chiral compound to form a salt. A preferred chiral compound is (+)-ephedrine. In the second step, step 8 of Scheme 1, the salt is reacted with a compound that aids in forming an amide bond. Examples of compounds that can be used to form an amide bond (i.e., amide forming reagents) are well known to those skilled in the art and include compounds that activate a carboxylic acid toward amide formation such as by conversion of the acid to an active ester, acid chloride, anhydride, etc. Examples of suitable regents include acid chlorides, acid anhydrides, chloroformates, thionyl chloride, phosphorus oxychloride, substituted carbodiimides, phosphoric acid, and the like. An especially preferred reagent is carbonyldiimidazole. It is noted that steps 7 and 8 can be run sequentially without isolation of intermediate products.

(+)-2-(7-Chloro-1,8-naphthyridin-2-yl)-3-(5-methyl-2-oxohexyl)-1-isoindolinone (8)

A solution of 2-{1-[(7-chloro-1,8-naphthyridin-2-yl)amino]-6-methyl-3-oxoheptyl}benzoic acid (74.9 kg, 175.9 mol), (1S, 2R)-ephedrine hemihydrate (32.5 kg, 186.5 mol), 200 proof ethanol (290 Kg) and water (17 L) were stirred and heated to about 35° C. for 35 minutes. The solution was filtered and then cooled to about 20° C. until the onset of crystallization. The reaction was further cooled to 0-5° C. for about 2 hours. The intermediate ephedrine salt was filtered and washed with a cold (0-5° C.) solution of 200 proof ethanol (206 Kg) and water (10 L). The ephedrine salt was dissolved in 377 L of dichloromethane and stirred with 125

L water and 9.7 kg 37% hydrochloric acid. The aqueous layer was removed. The organic layer was washed with water (125 L). The organic layer was distilled to 60% of the original volume. Carbonyldiimidazole was dissolved in CH₂Cl₂ (128 L) and slowly transferred to the reaction solution. The reaction was complete after 20 minutes. The reaction was washed two times with water (250 L each). The CH₂Cl₂ solution was distilled atmospherically, the volume being replaced with of 200 proof ethanol (500 Kg). The ethanol solution was cooled at a rate of 20±5° C. per hour to 0-5° C. The solution was then held at 0-5° C. for 16 hours. The product was filtered and washed with 200 proof ethanol (100 kg). The product was dried for 16 hours under vacuum at 60° C. This afforded 26.0 Kg of (+)-2-(7-chloro-1,8-naphthyridin-2-yl)-3-(5-methyl-2-oxohexyl)-1-isoindolinone as a white solid (36% yield). $^1$H-NMR: δ 8.87 (d, J=8.8, 1H), 8.61 (m, 2H), 7.93 (d, J=7.0, 1H), 7.74 (m, 4H), 6.05 (m, 1H), 3.62 (m, 1H), 3.28 (dd, J=7.0, 17.2, 1H), 2.42 (m, 2H), 1.35 (m, 3H), 0.79 (d, J=6.2, 6H); CI (MS) M+1 at 408, 100%; $[\alpha]_D^{20}$=+135° (c=1, dichloromethane).

The resolution of racemic 2-(7-chloro-1,8-naphthyridin-2-yl)-3-(5-methyl-2-oxohexyl)-1-isoindolinone by ring opening, resolution with a resolving agent, and then ring closure to give (+)-2-(7-chloro-1,8-naphthyridin-2-yl)-3-(5-methyl-2-oxohexyl)-1-isoindolinone is described in U.S. Pat. No. 5,498,716. Other resolution procedures, including resolving racemic 2-(7-chloro-1,8-naphthyridin-2-yl)-3-(5-methyl-2-oxohexyl)-1-isoindolinone directly to (+)-2-(7-chloro-1,8-naphthyridin-2-yl)-3-(5-methyl-2-oxohexyl)-1-isoindolinone without opening the lactam ring are known to those skilled in the art. Any resolution procedure is contemplated herein in conjunction with the synthesis of racemic 2-(7-chloro-1,8-naphthyridin-2-yl)-3-(5-methyl-2-oxohexyl)-1-isoindolinone. In other words, once racemic 2-(7-chloro-1,8-naphthyridin-2-yl)-3-(5-methyl-2-oxohexyl)-1-isoindolinone is made, various resolution procedures can be used by one skilled in the art to obtain (+)-2-(7-chloro-1,8-naphthyridin-2-yl)-3-(5-methyl-2-oxohexyl)-1-isoindolinone.

All documents referenced herein, including patents and patent applications, are hereby incorporated by reference. The following abbreviations are used herein.
Et₃N Triethylamine
HOAc Acetic Acid
DMF Dimethylformamide
cat. Catalytic amount
DME Dimethyl ether
THF Tetrahydrofuran
EtOH Ethanol
CDI Carbonyldiimidazole
MeOH Methanol
MTBE Methyl tert-butyl ether
MS Mass Spectra
NMR Nuclear Magnetic Resonance
DMSO Dimethylsulfoxide

What is claimed is:
1. A method of making 2-amino-7-hydroxy-1,8-naphthyridine sulfuric acid salt, the method comprising the steps of
   (a) dissolving 2,6-diaminopyridine in sulfuric acid to form a solution; and
   (b) adding malic acid to the solution to obtain 2-amino-7-hydroxy-1,8-naphthyridine sulfuric acid salt.
2. A method of making racemic 2-(7-chloro-1,8-naphthyridin-2-yl)-3-(5-methyl-2-oxohexyl)-1-isoindolinone, the method comprising the steps of:

a) reacting 2-amino-7-hydroxy-1,8-naphthyridine sulfuric acid salt with a phthalyl reactant in a solvent to form phthalimidyl naphthyridine 2

b) reacting phthalimidyl naphthyridine 2 with a chlorinating agent to form chloride 3

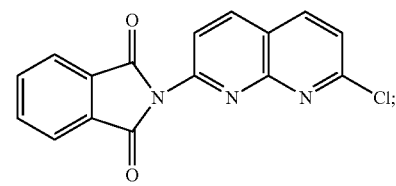

c) reacting chloride 3 with a reducing agent to form hydroxyindolinone 4

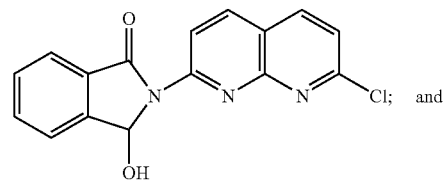

d) reacting hydroxyindolinone 4 with a 5-methyl-2-oxohexyl triphenyiphosphonium halide to form racemic 2-(7-chloro-1,8-naphthyridin-2-yl)-3-(5-methyl-2-oxohexyl)-1-isoindolinone.

3. The method of claim 2 wherein in step a the phthalyl reactant is phthalic anhydride; in step b the chlorinating agent is phosphorus oxychloride; in step c the reducing agent is potassium borohydride; and in step d the 5-methyl-2-oxo-hexyl derivative is [(5-methyl-2-oxo)-hexyl]triphenyiphosphonium bromide.

4. A method of making racemic 2-(7-chloro-1,8-naphthyridin-2-yl)-3-(5-methyl-2-oxohexyl)-1-isoindolinone, the method comprising the steps of:
a) reacting phthalimidyl naphthyridine 2

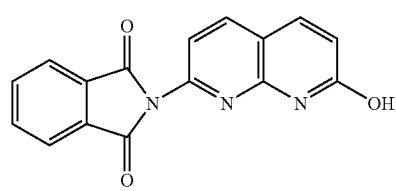

with a chlorinating agent to form chloride 3

3 b) reacting chloride 3 with a reducing agent to form hydroxyindolinone 4

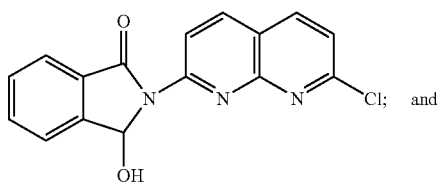

4 c) reacting hydroxyindolinone 4 with a 5-methyl-2-oxo-hexyltriphenylphosphonium halide to form racemic 2-(7-chloro-1,8-naphthyridin-2-yl)-3-(5-methyl-2-oxo-hexyl)-1-isoindolinone.

5. A method of making racemic 2-(7-chloro-1,8-naphthyridin-2-yl)-3-(5-methyl-2-oxohexyl)-1-isoindolinone, the method comprising the steps of:

a) reacting chloride 3

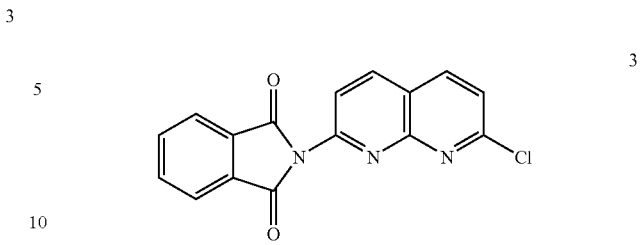

3 with a reducing agent to form hydroxyindolinone 4

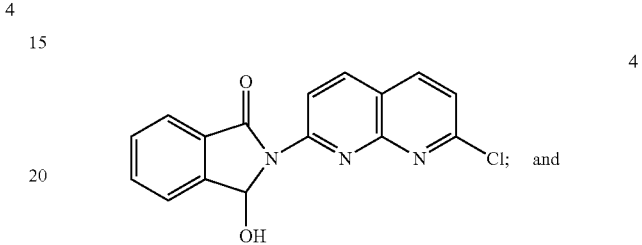

4 b) reacting hydroxyindolinone 4 with a 5-methyl-2-oxo-hexyltriphenylphosphonium halide to form racemic 2-(7-chloro-1,8-naphthyridin-2-yl)-3-(5-methyl-2-oxo-hexyl)-1-isoindolinone.

\* \* \* \* \*